(12) United States Patent
Luo et al.

(10) Patent No.: US 11,453,696 B2
(45) Date of Patent: *Sep. 27, 2022

(54) ADENOSINE ANALOGS AS METHYLTRANSFERASE INHIBITORS FOR TREATING CANCER

(71) Applicant: MEMORIAL SLOAN KETTERING CANCER CENTER, New York, NY (US)

(72) Inventors: Minkui Luo, New York, NY (US); Xiaochuan Cai, New York, NY (US); Ke Wang, New York, NY (US); Junyi Wang, New York, NY (US)

(73) Assignee: MEMORIAL SLOAN KETTERING CANCER CENTER, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/983,552

(22) Filed: Aug. 3, 2020

(65) Prior Publication Data

US 2021/0017216 A1 Jan. 21, 2021

Related U.S. Application Data

(63) Continuation of application No. 16/334,161, filed as application No. PCT/US2017/051858 on Sep. 15, 2017, now Pat. No. 10,730,903.

(60) Provisional application No. 62/396,318, filed on Sep. 19, 2016.

(51) Int. Cl.
- A61K 31/7076 (2006.01)
- C07H 19/167 (2006.01)
- C07H 19/16 (2006.01)

(52) U.S. Cl.
CPC ....... *C07H 19/167* (2013.01); *A61K 31/7076* (2013.01); *C07H 19/16* (2013.01)

(58) Field of Classification Search
None
See application file for complete search history.

(56) References Cited

U.S. PATENT DOCUMENTS

| | | | |
|---|---|---|---|
| 6,472,435 B1 | 10/2002 | Boyle | |
| 9,029,343 B2 | 5/2015 | Chesworth et al. | |
| 9,493,501 B2 | 11/2016 | Zheng et al. | |
| 10,730,903 B2* | 8/2020 | Luo | C07H 19/16 |
| 2015/0361037 A1 | 12/2015 | Tsaklakidis et al. | |
| 2016/0052955 A1 | 2/2016 | Luo et al. | |
| 2016/0137609 A1 | 5/2016 | Chesworth et al. | |

FOREIGN PATENT DOCUMENTS

| | | |
|---|---|---|
| WO | 2015013256 A1 | 1/2015 |
| WO | 2017070464 A1 | 4/2017 |

OTHER PUBLICATIONS

International Search Report and Written Opinion of the International Searching Authority for International Application No. PCT/US2017/051858 dated Dec. 1, 2017.

\* cited by examiner

*Primary Examiner* — Traviss C McIntosh, III
(74) *Attorney, Agent, or Firm* — Heslin Rothenberg Farley & Mesiti P.C.

(57) ABSTRACT

Compounds having methyltransferase inhibitory activity are disclosed. The compounds have the structures

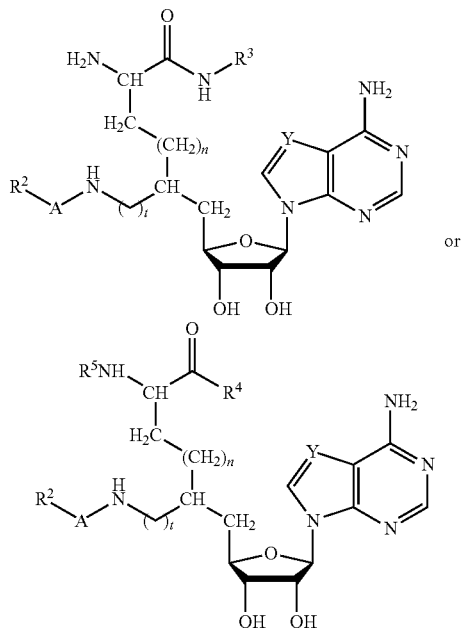

The compounds disclosed are useful in the treatment of cancer and similar diseases associated with inappropriate methyltransferase activity.

20 Claims, No Drawings

ADENOSINE ANALOGS AS METHYLTRANSFERASE INHIBITORS FOR TREATING CANCER

CROSS-REFERENCE TO RELATED APPLICATIONS

This application is a continuation of U.S. patent application Ser. No. 16/334,161, filed on Mar. 18, 2019, and published as US 2019-0276488 A1 on Sep. 12, 2019, which is a national stage filing under 35 U.S.C. § 371 of International Application No. PCT/US2017/051858, filed on Sep. 15, 2017, and published in English on Mar. 22, 2018 as WO 2018/053313 A1, and claims the benefit of priority to U.S. provisional application no. 62/396,318, filed on Sep. 19, 2016, the entire disclosures of all of which applications are hereby incorporated herein in their entireties.

GOVERNMENT RIGHTS STATEMENT

This invention was made with government support under GM396056 awarded by the National Institutes of Health. The government has certain rights in the invention.

FIELD OF THE INVENTION

This invention relates to chemical compounds having methyltransferase inhibitory activity and their use in the treatment of diseases and conditions associated with inappropriate methyltransferase activity.

BACKGROUND

Epigenetics is inheritable information not encoded in DNA manifested through control of gene expression, thereby controlling a range of cellular activity, including determining cell fate, stem cell fate and regulating proliferation. Epigenetic control over gene expression is accomplished in at least four ways: (1) covalent histone modification, (2) covalent DNA modification, (3) histone variation, and (4) nucleosome structure and DNA/histone contact points. Epigenetic control through one mechanism can influence the other suggesting a combinatorial regulation, as evidenced by the methylation of histones being implicated in the modulation of DNA methylation.

Covalent histone modifications, a key mechanism involved in epigenetic control, include: (1) lysine acetylation, (2) lysine and arginine methylation, (3) serine and threonine phosphorylation, (4) ADP-ribosylation, (5) ubiquitination, and (6) SUMOylation. Specific enzymatic activities are associated with these modifications and in the case of histone methylation, methyltransferases catalyze the transfer of a methyl group from cofactor S-adenosylmethionine to a lysine or arginine, producing S-adenosylhomocysteine as a by-product. Methyltransferases can also modify residues in other cellular proteins, e.g. the tumor suppressor p53.

Histone methyltransferases fall into subgroups that include arginine methyltransferases, SET-domain containing methyltransferases SU(VAR)3-9, E(Z) and TRX, and DOT-like methyltransferase hDOT1L. Families of SET-domain containing methyltransferases have been identified and include SUV39, SET1, SET2 and RIZ.

The disruption of the normal functions of methyltransferases has been implicated in human diseases. Members of different classes of methyltransferases are implicated in cancer and representative examples for the subgroups and subclasses are provided: (1) hDOT1L, a member of the DOT-like methyltransferases, is linked to leukemogenesis [Nature Cell Biology, 8:1017-1028 (2006); Cell, 121:167-178 (2005); Cell, 112:771-723 (2003)]. (2) EZH2, a SET1 methyltransferase, is up-regulated in tumor cell lines and has been linked to breast, gastric and prostate cancers [British Journal of Cancer, 90:761-769 (2004)]. (3) SUV39-1/2, SUV39 methyltransferases, have been linked to signaling pathways regulating cancer cell growth and differentiation [Genetica, 117(2-3):149-58 (2003)]. (4) NSD1, a SET2 subclass methyltransferase, has been linked to acute myeloid leukemia and Sotos syndrome, a predisposition to cancer [Molecular Cell Biology, 24(12):5184-96 (2004)]. (5) EVI1, a RIZ methyltransferase, is overexpressed in solid tumors and leukemia [Proceeding of the National Academy of Sciences, 93:1642-1647 (1996)]. (6) Related enzymes, namely SMYD2, are lysine methyltransferases that modify the tumor suppressor protein, p53 and through this activity, may function as an oncogene that interferes with p53's protective functions [Nature, 444(7119):629-632 (2006)]. (7) SMYD3, a SET-domain containing lysine methyltransferase, is involved in cancer cell proliferation [Nature Cell Biology, 6(8):731-740 (2004)]. (8) CARM1 (also known as PRMT4), an arginine methyltransferase, is linked to prostate cancer [Prostate, 66(12):1292-301 (2006)], breast cancer [Wang et al., Cancer Cell 25, 21-36, (2014)] and to myeloid leukemia [Vu et al., Cell Reports 5, 1625-1638, (2013)].

Inappropriate methyltransferase activities thus represent attractive targets for therapeutic intervention by small molecule inhibitors. In fact, inhibitors of SUV(AR) histone methyltransferase [Nature Chemical Biology, 1:143-145 (2005)] and protein arginine methyltransferase [Journal of Biological Chemistry, 279:23892-23899 (2004)] have been described. The present invention relates to novel synthetic compounds effective as inhibitors of inappropriate histone methyltransferase activities. As a consequence of their inhibition of histone methyltransferase activity, these compounds would be useful in treating human diseases, such as cancer, particularly breast cancer, prostate cancer and hematological malignancies, such as leukemias and lymphomas, e.g. acute and chronic lymphoblastic and myelogenous leukemia, as well as Hodgkin's and non-Hodgkin's lymphomas

BRIEF SUMMARY OF THE INVENTION

In one aspect, the invention relates to compounds of general formulae I and II, which are potent and selective inhibitors of lysine and arginine methyltransferase:

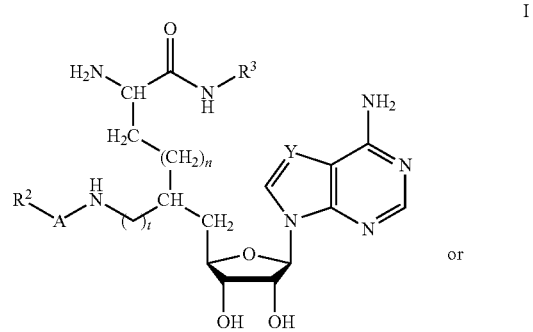

or

-continued

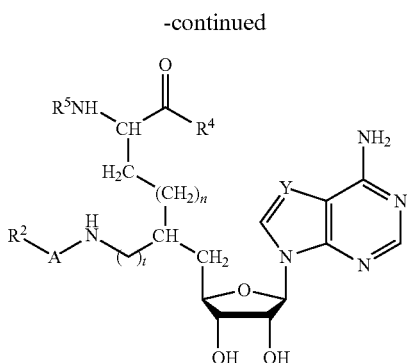

II wherein:
A is chosen from a direct bond and a $(C_1\text{-}C_{10})$hydrocarbon;
Y is N or CH;
$R^2$ is chosen from —H, and optionally substituted aryl and heteroaryl;
$R^3$ is chosen from
—$((CH_2)_m)$aryl substituted with one to three substituents chosen independently from $(C_1\text{-}C_6)$alkoxy, halo$(C_1\text{-}C_6)$alkoxy, methylenedioxy, ethylendioxy, $(C_1\text{-}C_6)$acyl, $(C_1\text{-}C_6)$alkoxyalkyl, hydroxy$(C_1\text{-}C_6)$alkyl, hydroxy, carboxy, —C(=O)O—$(C_1\text{-}C_6)$alkyl], carboxamido, acetoxy, amino, $(C_1\text{-}C_6)$alkylamino, di$(C_1\text{-}C_6)$alkylamino, $(C_1\text{-}C_6)$alkylsulfonylamino, and arylsulfonylamino;
—$((CH_2)_m)$heteroaryl optionally substituted with one to four substituents chosen independently from $(C_1\text{-}C_6)$alkoxy, halo$(C_1\text{-}C_6)$alkoxy, methylenedioxy, ethylendioxy, $(C_1\text{-}C_6)$acyl, $(C_1\text{-}C_6)$alkoxyalkyl, hydroxy$(C_1\text{-}C_6)$alkyl, hydroxy, carboxy, —C(=O)O—$(C_1\text{-}C_6)$alkyl], carboxamido, acetoxy, amino, $(C_1\text{-}C_6)$alkylamino, di$(C_1\text{-}C_6)$alkylamino, $(C_1\text{-}C_6)$alkylsulfonylamino, and arylsulfonylamino;
$R^4$ is chosen from —OH, —NH$((CH_2)_m)$aryl and —NH$((CH_2)_m)$heteroaryl, each said —NH$((CH_2)_m)$aryl or —NH$((CH_2)_m)$heteroaryl optionally substituted with one to three substituents chosen independently from $(C_1\text{-}C_6)$alkoxy, halo$(C_1\text{-}C_6)$alkoxy, methylenedioxy, ethylendioxy, $(C_1\text{-}C_6)$acyl, $(C_1\text{-}C_6)$alkoxyalkyl, hydroxy$(C_1\text{-}C_6)$alkyl, hydroxy, carboxy, —C(=O)O—$(C_1\text{-}C_6)$alkyl], carboxamido, acetoxy, amino, $(C_1\text{-}C_6)$alkylamino, di$(C_1\text{-}C_6)$alkylamino, $(C_1\text{-}C_6)$alkylsulfonylamino, and arylsulfonylamino;
$R^5$ is

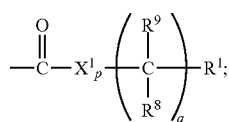

$X^1$ is chosen from O, N, and S(=O)$_2$,
$R^1$ is chosen from hydrogen, $C_1\text{-}C_{20}$ hydrocarbyl, $C_1\text{-}C_{20}$ oxaalkyl, $C_1\text{-}C_{20}$ thiaalkyl, $C_1\text{-}C_{20}$ azaalkyl, an optionally substituted benzoquinone, an optionally substituted hydrobenzoquinone, and phenyl substituted with at least one oxygenated substituent;
$R^8$ and $R^9$ are chosen independently in each occurrence from H and $(C_1\text{-}C_3)$alkyl;
m is 0 or an integer from 1 to 10;
n is 1 or 2;

p is an integer from 0 to 1 and q is an integer from 1 to 4, such that the sum of p and q is an integer from 1 to 4; and
t is 0, 1, or 2.

In another aspect, the invention relates to a compound of formula III, which is a potent and selective inhibitor of lysine and arginine methyltransferase:

Formula III

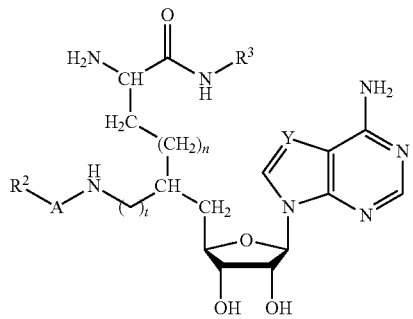

wherein:
Y is N;
A is a direct bond and $R^2$ is benzyl, such that $R^2$-A together are benzyl;
t is 0.
n is 1; and
$R^3$ is —CH$_3$.

In another aspect, the invention relates to methods of inhibiting the activity of a methyltransferase enzyme comprising contacting methyltransferase enzyme with at least one compound of general formula I, II, or III.

In another aspect, the invention relates to methods of treating cancer in a subject comprising administering to said subject a therapeutically effective amount of at least one compound of general formula I, II, or III.

In another aspect, the invention relates to pharmaceutical compositions comprising at least one compound of general formula I II, or III, and a pharmaceutically acceptable excipient.

DETAILED DESCRIPTION OF THE INVENTION

Throughout this specification, the substituents are defined when introduced and retain their definitions.

In one aspect, the invention relates to compounds having general formula I:

I

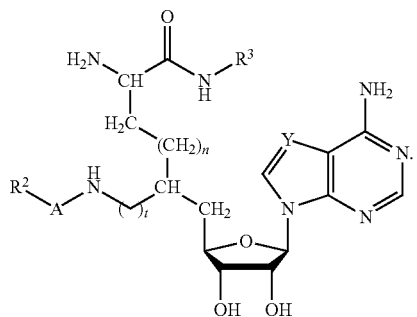

In some embodiments of formula I, A may be a direct bond or a $(C_1-C_{10})$hydrocarbon. In some embodiments, Y may be a N or CH. In some embodiments, $R^2$ may be chosen from —H, aryl, and heteroaryl. For example, $R^2$ may be benzyl and A may be a direct bond such that $R^2$-A together are benzyl. In some embodiments, $R^3$ may be a —$((CH_2)_m)$aryl substituted with one to three substituents chosen independently from $(C_1-C_6)$alkoxy, halo$(C_1-C_6)$alkoxy, methylenedioxy, ethylendioxy, $(C_1-C_6)$acyl, $(C_1-C_6)$alkoxyalkyl, hydroxy$(C_1-C_6)$alkyl, hydroxy, carboxy, —C(=O)O—$(C_1-C_6)$alkyl], carboxamido, acetoxy, amino, $(C_1-C_6)$alkylamino, di$(C_1-C_6)$alkylamino, $(C_1-C_6)$alkylsulfonylamino, and arylsulfonylamino. In some embodiments, $R^3$ may be —$((CH_2)_m)$heteroaryl optionally substituted with one to four substituents chosen independently from $(C_1-C_6)$alkoxy, halo$(C_1-C_6)$alkoxy, methylenedioxy, ethylendioxy, $(C_1-C_6)$acyl, $(C_1-C_6)$alkoxyalkyl, hydroxy$(C_1-C_6)$alkyl, hydroxy, carboxy, —C(=O)O—$(C_1-C_6)$alkyl], carboxamido, acetoxy, amino, $(C_1-C_6)$alkylamino, di$(C_1-C_6)$alkylamino, $(C_1-C_6)$alkylsulfonylamino, and arylsulfonylamino. In some embodiments, m may be 0 or an integer from 1 to 10. In some embodiments, n may be 1 or 2.

In some embodiments of formula I, m may be 0, 1, 2, 3, or 4. In some embodiments of formula I, m may be 1, 2, or 3. In some embodiments of formula I, m is 1 or 2.

In some embodiments of formula I, t may be 0, 1 or 2. In some embodiments of formula I, t is 1.

In some embodiments of formula I, Y may be an N. In some embodiments, A may be —$CH_2$—. In some embodiments, $R^2$ may be a phenyl.

In some embodiments of formula I, Y may be an N, A may be —$CH_2$—, $R^2$ may be a phenyl, and t may be 1; these fall into a genus of formula Ia:

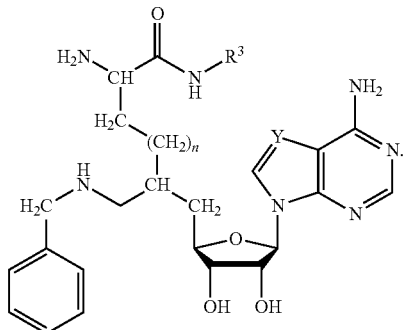

Ia

In some embodiments of formula Ia, $R^3$ may be —$((CH_2)_m)$aryl substituted with one to three substituents chosen independently from —O$((C_1-C_3)$alkyl), —O$((CH)R^6 R^7)$, methylenedioxy, ethylendioxy, and halogen. In some embodiments, $R^6$ and $R^7$ may independently be chosen from H and halogen. In some embodiments, m may be 0 or an integer from 1 to 10. In some embodiments, m may be 0, 1, 2, 3, 4, or 5. In some embodiments, m may be 1, 2, or 3. In some embodiments m may be 1 or 2. In some embodiments, n may be 1 or 2. For example, in some embodiments, $R^3$ may be —$((CH_2)_m)$phenyl substituted with one to three substituents chosen independently from —$OCH_3$, —$OCHF_2$ and halogen, and n may be 2.

In some embodiments of formula Ia, $R^3$ may be —$((CH_2)_m)$heteroaryl optionally substituted with one to four substituents chosen independently from —O$((C_1-C_3)$alkyl), —O$((CH)R_6 R_7)$, $(C_1-C_{20})$hydrocarbon, methylenedioxy, ethylendioxy, and halogen. In some embodiments, $R^6$ and $R^7$ may independently be chosen from H and halogen. In some embodiments, m may be 0 or an integer from 1 to 10. In some embodiments, m may be 0, 1, 2, 3, 4, or 5. In some embodiments, m may be 1, 2, or 3. In some embodiments m may be 1 or 2. In some embodiments, n may be 1 or 2. For example, in some embodiments, $R^3$ may be —$((CH_2)_m)$heteroaryl optionally substituted with one to four substituents chosen independently from —O$((C_1-C_3)$alkyl), —O$((CH)R^6 R^7)$ and $(C_1-C_{20})$hydrocarbon, wherein said —$((CH_2)_m)$heteroaryl is a nitrogen heteroaryl. For example, in some embodiments of formula Ia, $R^3$ may be —$((CH_2)_2)$phenyl substituted with one to three substituents chosen independently from —$OCH_3$, —$OCHF_2$ and halogen, and n may be 2.

In some embodiments of formula Ia, $R^3$ may be

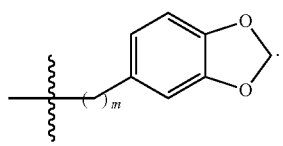

In some embodiments, $R^3$ may be

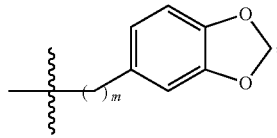

m may be 2, and n may be 2.

In another aspect, the invention relates to compounds having general formula II:

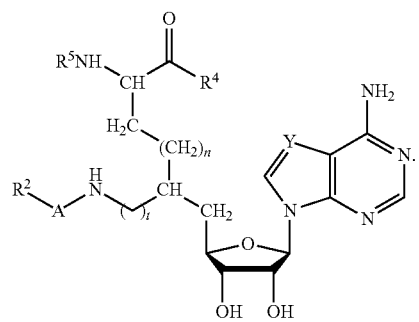

II

In some embodiments of formula II, A may be a direct bond or a $(C_1-C_{10})$hydrocarbon. In some embodiments, Y may be an N or CH. In some embodiments, $R^2$ may be chosen from —H, aryl, and heteroaryl. In some embodiments, $R^5$ may be

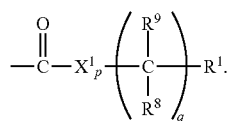

In some embodiments, $X^1$ may be chosen from O, N, and $S(=O)_2$. In some embodiments, $R^1$ may be chosen from hydrogen, $C_1$-$C_{20}$ hydrocarbyl, $C_1$-$C_{20}$ oxaalkyl, $C_1$-$C_{20}$ thiaalkyl, $C_1$-$C_{20}$ azaalkyl, an optionally substituted benzoquinone, an optionally substituted hydrobenzoquinone, and phenyl substituted with at least one oxygenated substituent. In some embodiments, $R^8$ and $R^9$ may be chosen independently in each occurrence from H and $(C_1$-$C_3)$alkyl. In some embodiments, m may be 0 or an integer from 1 to 10. In some embodiments, n may be 1 or 2. In some embodiments, p may be an integer from 0 to 1 and q may be an integer from 1 to 4, such that the sum of p and q may be an integer from 1 to 4.

In some embodiments of formula II, m may be 0, 1, 2, 3, or 4. In some embodiments of formula II, m may be 1, 2, or 3. In some embodiments of formula II, m is 1 or 2.

In some embodiments of formula II, t may be 0, 1 or 2. In some embodiments of formula II, t is 1.

In some embodiments of formula II, Y may be an N. In some embodiments, A may be —$CH_2$—. In some embodiments, $R^2$ may be a phenyl. For example, $R^2$ may be benzyl and A may be a direct bond such that $R^2$-A together are benzyl. In some embodiments, $R^1$ may be

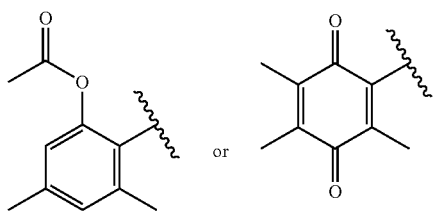

In some embodiments of formula II, Y may be an N, A may be —$CH_2$—, $R^2$ may be a phenyl, and t may be 1; these fall into a genus of formula IIa:

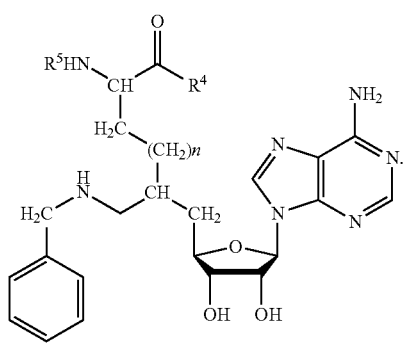

IIa

In some embodiments of formula IIa, $R^4$ may be chosen from —OH, —$NH((CH_2)_m)$aryl or —$NH((CH_2)_m)$heteroaryl, each said —$NH((CH_2)_m)$aryl or —$NH((CH_2)_m)$heteroaryl may be optionally substituted with one to three substituents chosen independently from a halogen, —O(($C_1$-$C_3$)alkyl), —O(($CH)R_6 R_7$), ($C_1$-$C_{20}$)hydrocarbon, methylenedioxy, ethylenedioxy, and halogen. In some embodiments, $R^6$ and $R^7$ may independently be chosen from H and halogen. In some embodiments, m may be 0 or an integer from 1 to 10. In some embodiments, m may be 0, 1, 2, 3, 4, or 5. In some embodiments, m may be 1, 2, or 3. In some embodiments m may be 1 or 2. In some embodiments, n may be 1 or 2. For example, in some embodiments, $R^4$ may be chosen from —OH and —$NH((CH_2)_m)$phenyl, where said —$NH((CH_2)_m)$phenyl may be optionally substituted with one to three substituents chosen independently from halogen, —O(($C_1$-$C_3$)alkyl), —O(($CH)R^6 R^7$), and ($C_1$-$C_{20}$) hydrocarbon.

In some embodiments of formula IIa, $R^5$ may be

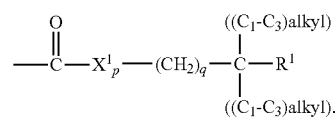

In some embodiments, $X^1$ may be O, N, or $S(=O)_2$. In some embodiments, p may be an integer from 0 to 1 and q may be an integer from 0 to 3, such that the sum of p and q may be an integer from 0 to 3. In some embodiments, $R^1$ may be chosen from hydrogen, $C_1$-$C_{20}$ hydrocarbyl, $C_1$-$C_{20}$ oxaalkyl, $C_1$-$C_{20}$ thiaalkyl, $C_1$-$C_{20}$ azaalkyl, an optionally substituted benzoquinone, an optionally substituted hydrobenzoquinone, and phenyl substituted with at least one oxygenated substituent. In some embodiments, q may be an integer from 1 to 4. For example, in some embodiments, p may be 0 and $R^1$ may be

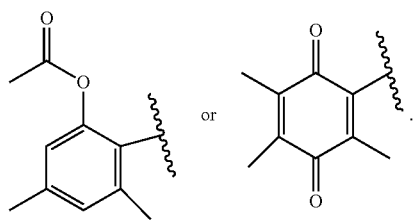 [SMILES: *c1c(C)cc(C)cc1OC(C)=O ; *C1=C(C)C(=O)C(C)=C(C)C1=O]

For example, in some embodiments of formula IIa, $R^4$ may be —OH, $R^5$ may be

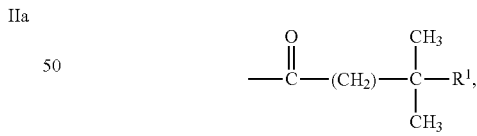

$R^1$ may be

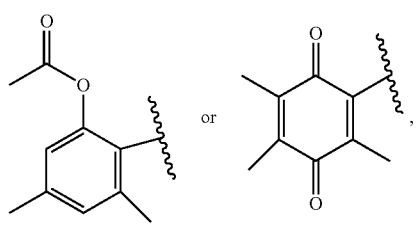 [SMILES: *c1c(C)cc(C)cc1OC(C)=O ; *C1=C(C)C(=O)C(C)=C(C)C1=O]

and n may be 2.

As an another example, in some embodiments of formula IIa, R⁴ may be —NH((CH₂)₂)phenyl that may be optionally substituted with one to three substituents chosen independently from —OCH₃, —OCHF₂, and phenyl, R⁵ may be

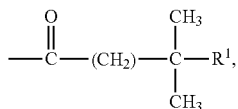

and R¹ may be

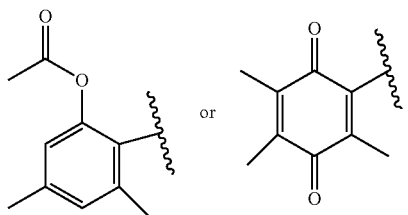

The members of these genera are effective as inhibitors of methyltransferase activities and therefore, are useful for the inhibition, prevention and suppression of various pathologies associated with such activities, such as, for example, cancer cell and cancer stem cell fate differentiation, and cancer cell proliferation and cell cycle regulation. The compounds are also useful research tools for studying protein methyl transferase biology.

For convenience and clarity, certain terms employed in the specification, examples, and claims are described herein.

Unless otherwise specified, alkyl is intended to include linear or branched saturated hydrocarbon structures and combinations thereof. Alkyl refers to alkyl groups of from 1 to 20 carbon atoms, preferably 1 to 10 carbon atoms, more preferably 1 to 6 carbon atoms. Examples of alkyl groups include methyl, ethyl, propyl, isopropyl, n-butyl, s-butyl, t-butyl and the like.

Cycloalkyl is a subset of hydrocarbon and includes cyclic hydrocarbon groups of from 3 to 8 carbon atoms. Examples of cycloalkyl groups include c-propyl, c-butyl, c-pentyl, norbornyl and the like.

$C_1$ to $C_{20}$ hydrocarbon includes alkyl, cycloalkyl, polycycloalkyl, alkenyl, alkynyl, aryl and combinations thereof. Examples include benzyl, phenethyl, propargyl, allyl, cyclohexylmethyl, adamantyl, camphoryl and naphthylethyl. Hydrocarbon refers to any substituent comprised of hydrogen and carbon as the only elemental constituents.

Unless otherwise specified, the term "carbocycle" is intended to include ring systems in which the ring atoms are all carbon but of any oxidation state. Thus ($C_3$-$C_{12}$) carbocycle refers to both non-aromatic and aromatic systems, including such systems as cyclopropane, benzene and cyclohexene. Carbocycle, if not otherwise limited, refers to monocycles, bicycles and polycycles. ($C_8$-$C_{12}$) Carbopolycycle refers to such systems as norbornane, decalin, indane and naphthalene.

Alkoxy or alkoxyl refers to groups of from 1 to 20 carbon atoms, preferably 1 to 10 carbon atoms, more preferably 1 to 6 carbon atoms of a straight or branched configuration attached to the parent structure through an oxygen. Examples include methoxy, ethoxy, propoxy, isopropoxy and the like.

Oxaalkyl refers to alkyl residues in which one or more carbons (and their associated hydrogens) have been replaced by oxygen. Examples include methoxypropoxy, 3,6,9-trioxadecyl and the like. The term oxaalkyl is intended as it is understood in the art [see Naming and Indexing of Chemical Substances for Chemical Abstracts, published by the American Chemical Society, 2002 edition, ¶196, but without the restriction of 127(a)], i.e. it refers to compounds in which the oxygen is bonded via a single bond to its adjacent atoms (forming ether bonds); it does not refer to doubly bonded oxygen, as would be found in carbonyl groups. Similarly, thiaalkyl and azaalkyl refer to alkyl residues in which one or more carbons has been replaced by sulfur or nitrogen, respectively. Examples of azaalkyl include ethylaminoethyl and aminohexyl.

Heterocycle means a cycloalkyl or aryl carbocyclic residue in which from one to four carbons is replaced by a heteroatom selected from the group consisting of N, O and S. Heteroaryl is a subset of heterocycle in which the heterocycle is aromatic. Examples of heteroaromatic rings include: furan, benzofuran, isobenzofuran, pyrrole, indole, isoindole, thiophene, benzothiophene, imidazole, benzimidazole, purine, pyrazole, indazole, oxazole, benzoxazole, isoxazole, benzisoxazole, thiazole, benzothiazole, triazole, tetrazole, pyridine, quinoline, isoquinoline, pyrazine, quinoxaline, acridine, pyrimidine, quinazoline, pyridazine, cinnoline, phthalazine, and triazine.

As used herein, the term "optionally substituted" may be used interchangeably with "unsubstituted or substituted". The term "substituted" refers to the replacement of one or more hydrogen atoms in a specified group with a specified radical. For example, substituted alkyl, aryl, cycloalkyl, heterocyclyl etc. refer to alkyl, aryl, cycloalkyl, or heterocyclyl wherein one or more H atoms in each residue are replaced with halogen, haloalkyl, alkyl, acyl, alkoxyalkyl, hydroxyloweralkyl, carbonyl, phenyl, heteroaryl, benzenesulfonyl, hydroxy, loweralkoxy, haloalkoxy, oxaalkyl, carboxy, alkoxycarbonyl [—C(═O)O-alkyl], alkoxycarbonylamino [HNC(═O)O-alkyl], carboxamido [—C(═O)NH₂], alkylaminocarbonyl [—C(═O)NH-alkyl], cyano, acetoxy, nitro, amino, alkylamino, dialkylamino, (alkyl)(aryl)aminoalkyl, alkylaminoalkyl (including cycloalkylaminoalkyl), dialkylaminoalkyl, dialkylaminoalkoxy, heterocyclylalkoxy, mercapto, alkylthio, sulfoxide, sulfone, sulfonylamino, alkylsulfinyl, alkylsulfonyl, alkylsulfonylamino, arylsulfonyl, arylsulfonylamino, acylaminoalkyl, acylaminoalkoxy, acylamino, amidino, aryl, benzyl, heterocyclyl, heterocyclylalkyl, phenoxy, benzyloxy, heteroaryloxy, hydroxyimino, alkoxyimino, oxaalkyl, aminosulfonyl, trityl, amidino, guanidino, ureido, benzyloxyphenyl, and benzyloxy. "Oxo" is also included among the substituents referred to in "optionally substituted"; it will be appreciated by persons of skill in the art that, because oxo is a divalent radical, there are circumstances in which it will not be appropriate as a substituent (e.g. on phenyl). In one embodiment, 1, 2 or 3 hydrogen atoms are replaced with a specified radical. In the case of alkyl and cycloalkyl, more than three hydrogen atoms can be replaced by fluorine; indeed, all available hydrogen atoms could be replaced by fluorine. Such compounds (e.g. perfluoroalkyl) fall within the class of "fluorohydrocarbons". To be clear, a generic term may encompass more than one substituent, that is, for example, "haloalkyl" or "halophenyl" refers to an alkyl or phenyl in which at least one, but perhaps more than one, hydrogen is replaced by halogen. In preferred embodiments, substituents are halogen, haloalkyl, alkyl, acyl, hydroxyalkyl, hydroxy, alkoxy, haloalkoxy, oxaalkyl, carboxy, cyano, acetoxy, nitro, amino, alkylamino, dialkylamino, alkylthio, alkylsulfinyl, alkylsulfonyl, alkylsulfonylamino arylsulfonyl, arylsulfonylamino and benzyloxy.

In describing compounds herein, the terminology "substituted with at least one oxygenated substituent" is used. An oxygenated substituent is a substituent that contains oxygen in addition to carbon and hydrogen; an oxygenated substituent may also include additional heteroatoms, such as nitrogen (for example, a carboxamide or methanesulfonyl). Typical examples of oxygenated substituents include alkoxy, hydroxy, fluoroalkoxy, formyl, acetyl and other $C_1$ to $C_6$ acyl chains.

Substituents $R^n$ are generally defined when introduced and retain that definition throughout the specification and in all independent claims.

As used herein, and as would be understood by the person of skill in the art, the recitation of "a compound"—unless expressly further limited—is intended to include salts of that compound. Thus, for example, the recitation "a compound of formula I" as depicted above, which incorporates a substituent COOH (e.g. $R^4$=OH), would include salts in which the substituent is $COO^-M^+$, wherein M is any counterion. Similarly, formula I as depicted above depicts a substituent $NH_2$, and therefore would also include salts in which the substituent is $NH_3^+ X^-$, wherein X is any counterion. Compounds containing a COOH substituent may commonly exist as zwitterions, which are effectively internal salts. In a particular embodiment, the term "compound of formula I" refers to the compound or a pharmaceutically acceptable salt thereof.

The term "pharmaceutically acceptable salt" refers to salts whose counter ion derives from pharmaceutically acceptable non-toxic acids and bases. Suitable pharmaceutically acceptable acids for salts of the compounds of the present invention include, for example, acetic, adipic, alginic, ascorbic, aspartic, benzenesulfonic (besylate), benzoic, boric, butyric, camphoric, camphorsulfonic, carbonic, citric, ethanedisulfonic, ethanesulfonic, ethylenediaminetetraacetic, formic, fumaric, glucoheptonic, gluconic, glutamic, hydrobromic, hydrochloric, hydroiodic, hydroxynaphthoic, isethionic, lactic, lactobionic, laurylsulfonic, maleic, malic, mandelic, methanesulfonic, mucic, naphthylenesulfonic, nitric, oleic, pamoic, pantothenic, phosphoric, pivalic, polygalacturonic, salicylic, stearic, succinic, sulfuric, tannic, tartaric acid, teoclatic, p-toluenesulfonic, and the like. Suitable pharmaceutically acceptable base addition salts for the compounds of the present invention include, but are not limited to, metallic salts made from aluminum, calcium, lithium, magnesium, potassium, sodium and zinc or organic salts made from lysine, arginine, N,N'-dibenzylethylenediamine, chloroprocaine, choline, diethanolamine, ethylenediamine, meglumine (N-methylglucamine) and procaine. Further pharmaceutically acceptable salts include, when appropriate, nontoxic ammonium cations and carboxylate, sulfonate and phosphonate anions attached to alkyl having from 1 to 20 carbon atoms.

It will be recognized that the compounds of this invention can exist in radiolabeled form, i.e., the compounds may contain one or more atoms containing an atomic mass or mass number different from the atomic mass or mass number usually found in nature. Alternatively, a plurality of molecules of a single structure may include at least one atom that occurs in an isotopic ratio that is different from the isotopic ratio found in nature. Radioisotopes of hydrogen, carbon, phosphorous, fluorine, chlorine and iodine include $^2H$, $^3H$, $^{11}C$, $^{13}C$, $^{14}C$, $^{15}N$, $^{35}S$, $^{18}F$, $^{36}C$, $^{125}I$, $^{124}I$ and $^{131}I$ respectively. Compounds that contain those radioisotopes and/or other radioisotopes of other atoms are within the scope of this invention. Tritiated, i.e. $^3H$, and carbon-14, i.e., $^{14}C$, radioisotopes are particularly preferred for their ease in preparation and detectability. Compounds that contain isotopes $^{11}C$, $^{13}N$, $^{15}O$, $^{124}I$ and $^{18}F$ are well suited for positron emission tomography. Radiolabeled compounds of formula I of this invention and prodrugs thereof can generally be prepared by methods well known to those skilled in the art. Conveniently, such radiolabeled compounds can be prepared by carrying out the procedures disclosed in the Examples and Schemes by substituting a readily available radiolabeled reagent for a non-radiolabeled reagent.

Persons of skill will readily appreciate that compounds described herein, when appropriately labeled as described above, can be employed in a method of identifying (i.e. labeling) specific methyltransferase enzymes in the presence of other enzymes, including other methyltransferase enzymes, for which their affinity is lower. Usually two orders of magnitude difference in affinity will be sufficient to distinguish between enzymes. Using methods well known to persons of skill in the art, specific methyltransferase enzymes can be localized in tissues, cells and organelles. A further aspect of the invention described herein is thus a method of identifying and/or localizing specific methyltransferase enzymes.

While it may be possible for the compounds of formula I or formula II to be administered as the raw chemical, it is preferable to present them as a pharmaceutical composition. According to a further aspect, the present invention provides a pharmaceutical composition comprising a compound of formula I, formula II, or a pharmaceutically acceptable salt or solvate thereof, together with one or more pharmaceutically carriers thereof and optionally one or more other therapeutic ingredients. The carrier(s) must be "acceptable" in the sense of being compatible with the other ingredients of the formulation and not deleterious to the recipient thereof. The compositions may be formulated for oral, topical or parenteral administration. For example, they may be given intravenously, intraarterially, subcutaneously, and directly into the CNS—either intrathecally or intracerebroventricularly.

Formulations include those suitable for oral, parenteral (including subcutaneous, intradermal, intramuscular, intravenous and intraarticular), rectal and topical (including dermal, buccal, sublingual and intraocular) administration. The compounds are preferably administered orally or by injection (intravenous or subcutaneous). The precise amount of compound administered to a patient will be the responsibility of the attendant physician. However, the dose employed will depend on a number of factors, including the age and sex of the patient, the precise disorder being treated, and its severity. Also, the route of administration may vary depending on the condition and its severity. The formulations may conveniently be presented in unit dosage form and may be prepared by any of the methods well known in the art of pharmacy. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

It should be understood that in addition to the ingredients particularly mentioned above, the formulations of this invention may include other agents conventional in the art having regard to the type of formulation in question, for example those suitable for oral administration may include flavoring agents.

As used herein, "treatment" or "treating," or "palliating" or "ameliorating" are used interchangeably herein. These terms refers to an approach for obtaining a therapeutic benefit in the form of eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. The compositions may be administered to a patient at risk of developing a particular disease, or to a patient reporting one or more of the physiological symptoms of a disease, even though a diagnosis of this disease may not have been made.

Terminology related to "protecting", "deprotecting" and "protected" functionalities occurs throughout this application. Such terminology is well understood by persons of skill in the art and is used in the context of processes that involve sequential treatment with a series of reagents. In that context, a protecting group refers to a group which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes described herein, the person of ordinary skill can readily envision those groups that would be suitable as "protecting groups". Suitable groups for that purpose are discussed in standard textbooks in the field of chemistry, such as Protective Groups in Organic Synthesis by T. W. Greene [John Wiley & Sons, New York, 1991], which is incorporated herein by reference.

A comprehensive list of abbreviations utilized by organic chemists appears in the first issue of each volume of the *Journal of Organic Chemistry*. The list, which is typically presented in a table entitled "Standard List of Abbreviations", is incorporated herein by reference.

In general, the compounds of the present invention may be prepared by the methods illustrated in general reaction schemes as, for example, described below, or by modifications thereof, using readily available starting materials, reagents and conventional synthesis procedures. In these reactions, it is also possible to make use of variants that are in themselves known, but are not mentioned here. The starting materials are either commercially available, synthesized as described in the examples or may be obtained by the methods well known to persons of skill in the art. In particular, methods appropriate to the synthesis of these compounds may be found in U.S. Pat. No. 9,493,501 and US published application number 2016-0052955, the disclosures of which are incorporated herein in their entireties by reference.

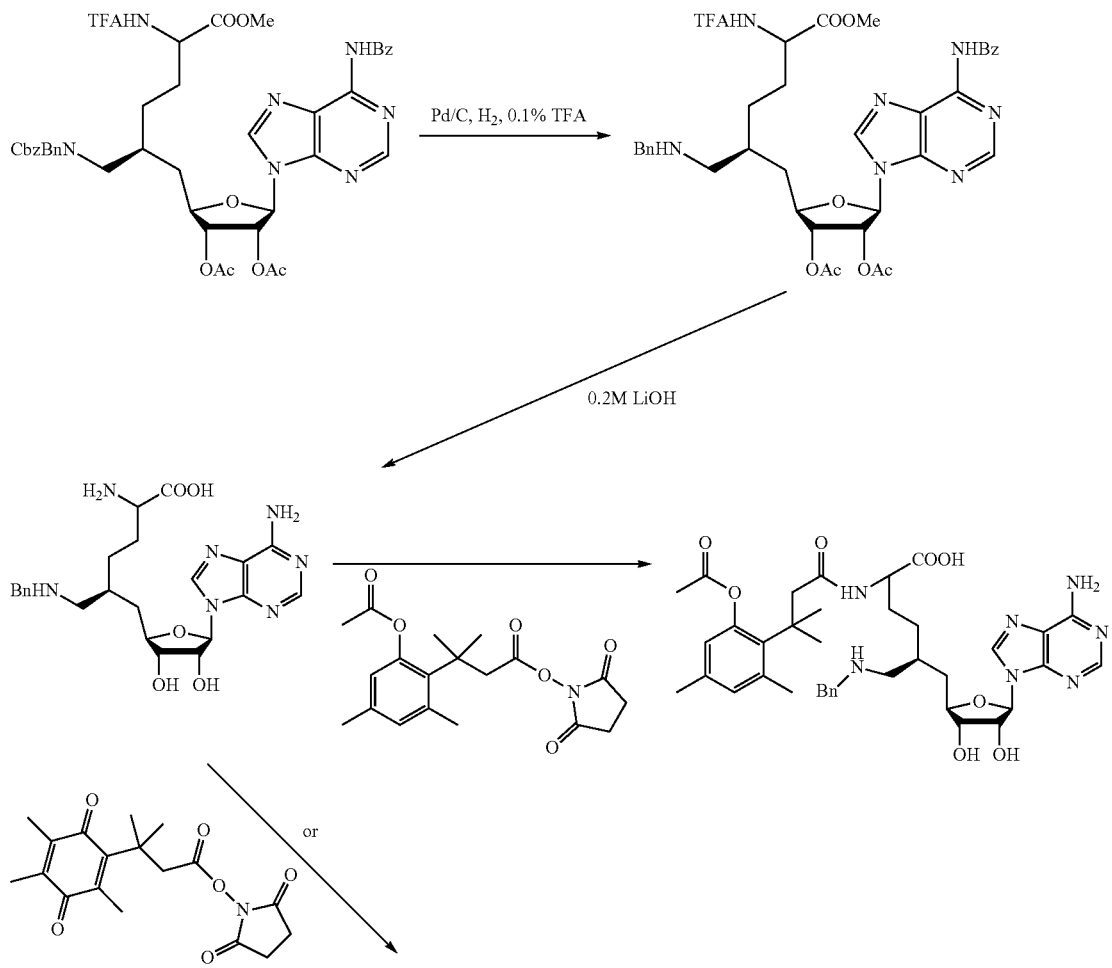

Scheme 1, synthesis of pro-drugs of amino-acid derivatives

-continued
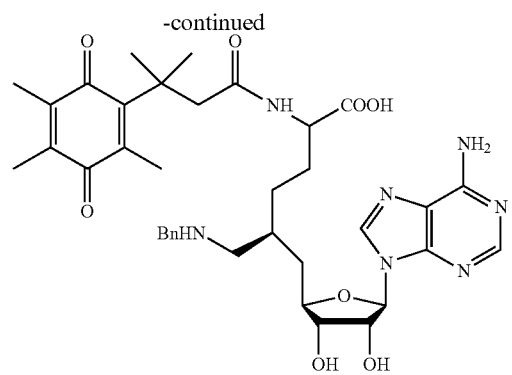
Scheme 2, synthesis of pro-drugs of amino-amide derivatives
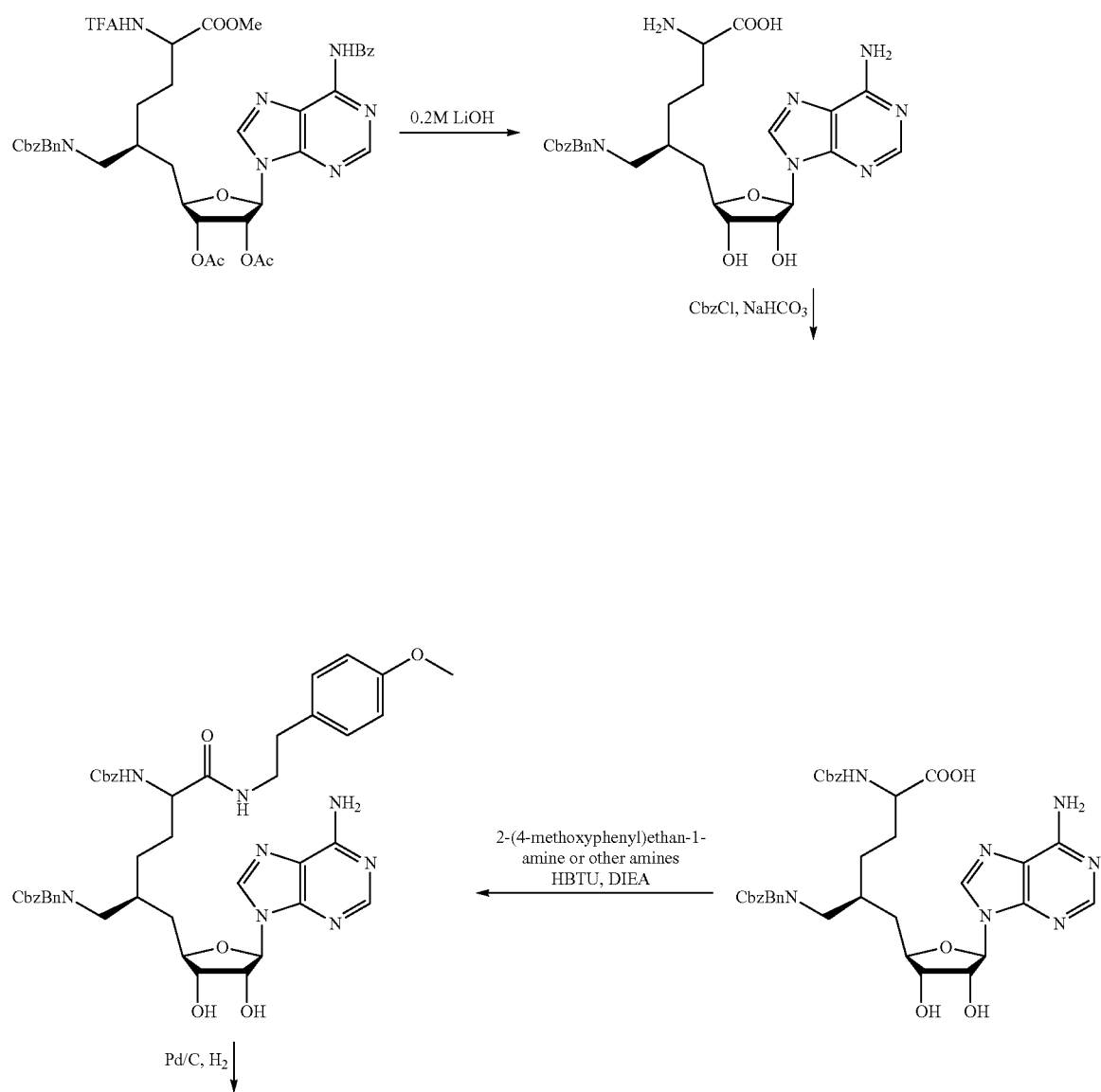

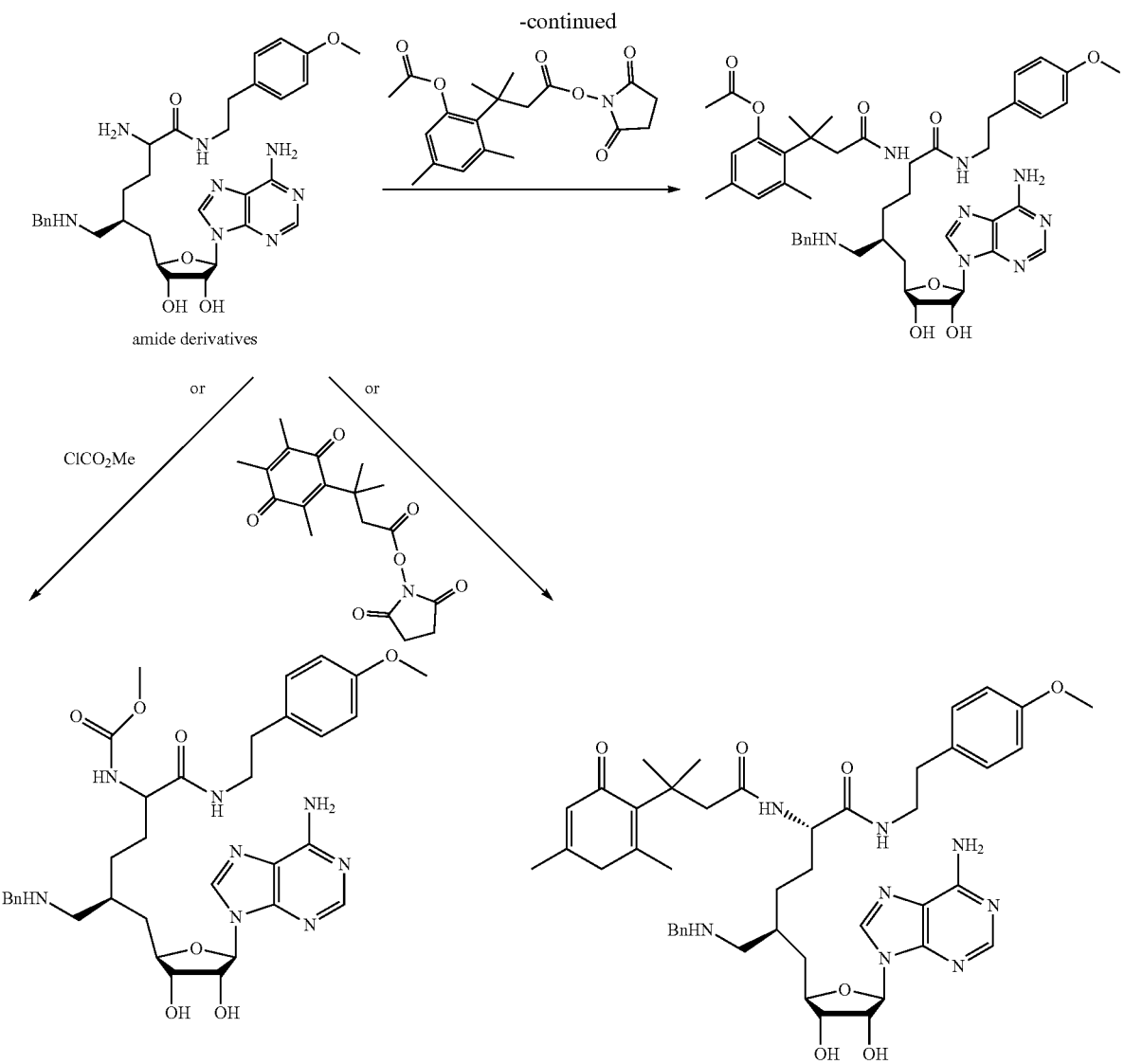
Specific examples of compounds of the present invention made via Schemes 1 or 2 above include:
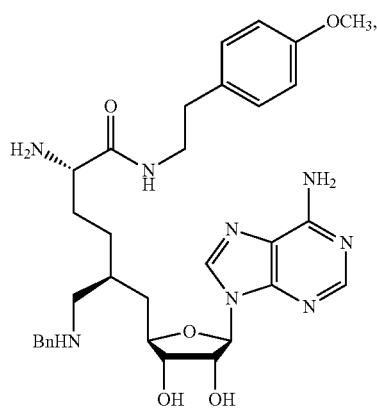
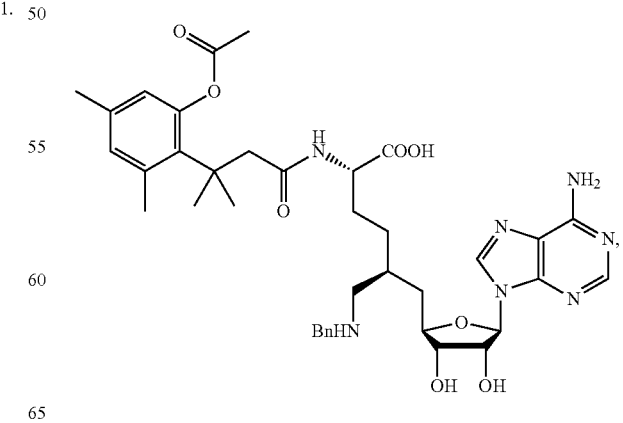

3.
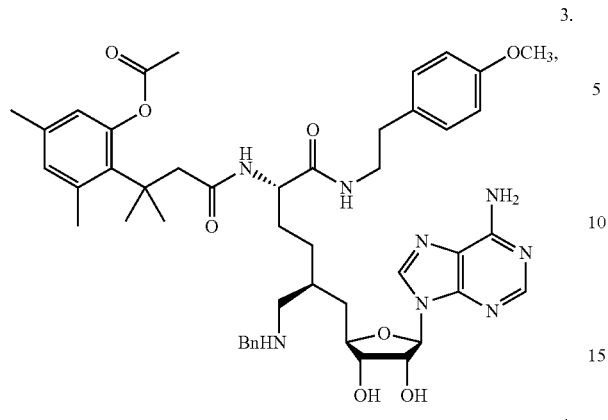
4.
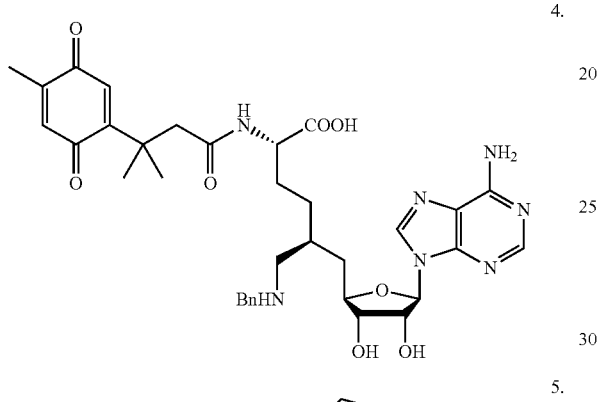
5.
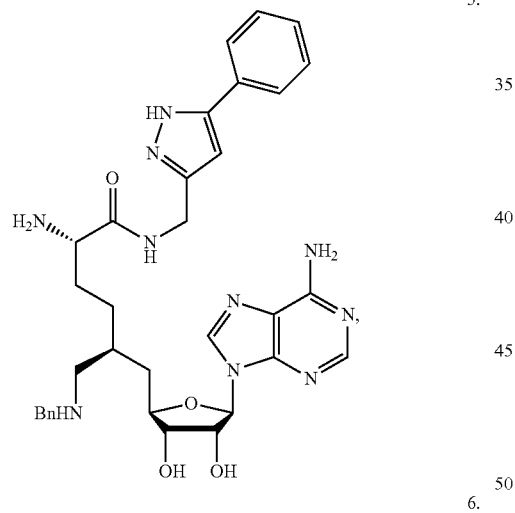
6.
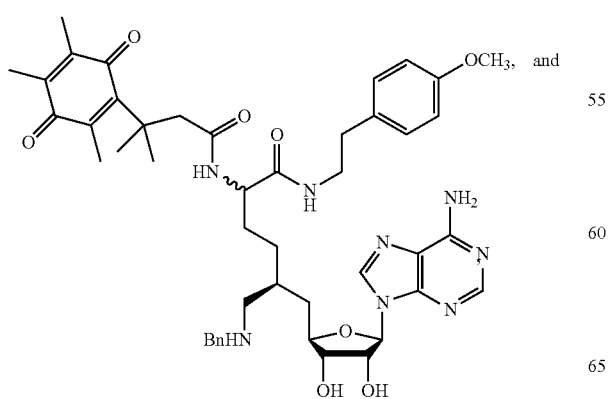
7.
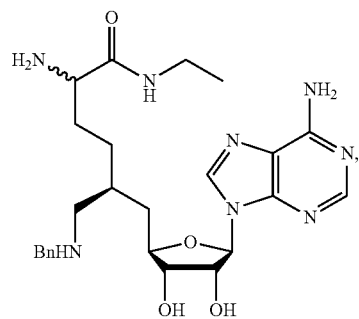
Additional examples include:
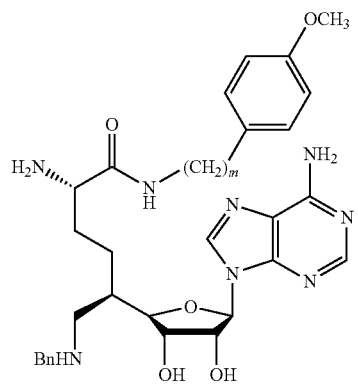
wherein m is 1, 3 and 4,
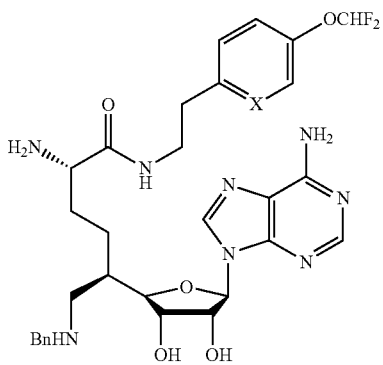

wherein X is N or CH,

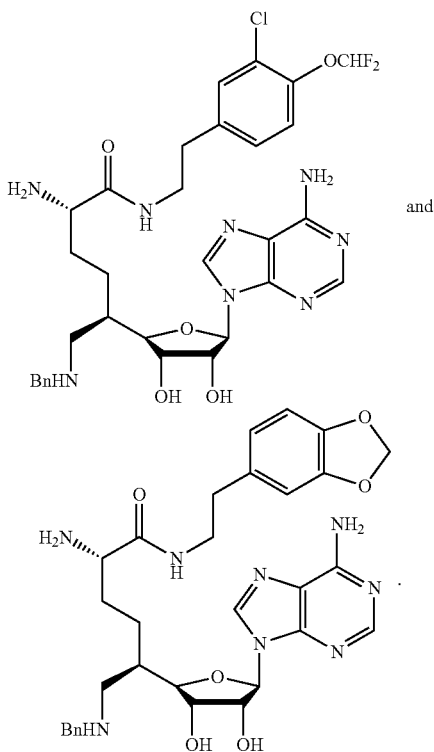

The compounds described above were tested as described below:

IC$_{50}$ Assay.

Filter-paper Assay. This assay relies on Whatman P-81 filter paper, which binds peptides but not SAM. Protein Methyl Transferases (PMTs) transfer $^3$H-Me of [$^3$H-Me]-SAM to peptide substrates and the resultant 3H-methylated, filter-paper-bound peptide is quantified with a scintillation counter. Briefly, 6 μL of the methylation reaction was spotted onto Whatman P-81 phosphocellulose filter paper (1.2×1.2 cm$^2$) to immobilize the $^3$H-labeled peptide. After drying in air for 20 min, the filter paper was immersed into 20 mL of 50 mM Na$_2$CO$_3$/NaHCO$_3$ buffer (pH=9.2), and washed 5 times for 10 min each time. The washed filter paper was then transferred to a 20 mL scintillation vial containing 1 mL of distilled water and 10 mL of Ultima Gold scintillation cocktail or 7 mL scintillation vial containing 0.5 mL od distilled water and 5 mL of scintillation cocktail (PerkinElmer). The radioactivity was quantified by a Beckman LS6000IC liquid scintillation counter.

Dose-response Curves and IC$_{50}$. Twice the PMT concentration was incubated for 10 min with varied concentration of inhibitors (0.1-400 μM stocks), into which 10 μl of the PMT peptide substrate and radioactive cofactor (3 μM of the corresponding peptide and 1.5 μM, 0.15 μCi [$^3$H-Me]-SAM) were added. After incubating the reaction mixture for the respective reaction time, the conversion was quantified with the filter paper assay as described above. The inhibition was expressed as the percentage between the high control (no inhibition) and the low control (no enzyme) as follows: Percentage Inhibition=[(high control-reading)/(high control-low control)]×100%. Each experiment was performed in triplicate. The IC$_{50}$ values were obtained by fitting inhibition percentage versus inhibitor concentration using GraphPad Prism5 software.

EC$_{50}$ Assay.

1~2×10e$^5$ MCF-7 cells or MDA-MB-231 cells per were seeded into 6-well plate. Two days later, cells were treated with inhibitors or control for additional two days. Then cells were collected by trypsinization, washed with Dulbecco's phosphate buffer saline and lysed by suspension in lysis buffer. The suspension was kept on ice for 30 min to achieve complete lysis or the suspension can be sonicated to achieve complete lysis. After centrifugation, supernatant were collected and total protein was quantified, and western blot samples were prepared with the SDS sample buffer Proteins were transferred to a nitrocellulose membrane for 1.5 hr at 350 mA at cold room. Membranes were blocked with 5% nonfat milk dissolved in PBST at room temperature for 1 hour and incubated overnight with primary antibody diluted in 5% nonfat milk dissolved in PBST at 4° C. Membranes were then washed with PBST for 10 min/each three times, and incubated with HRP-conjugated secondary antibody for 1 hour at room temperature, and washed with PBST for 10 min/each three times, and then detected by ECL reaction and X-ray film exposure. BAF155 and PABP1 were used as biomarkers to determine the EC$_{50}$ values.

The results of testing are shown in the following Table 1:

TABLE 1

| Example Number | IC$_{50}$ in μM | EC$_{50}$ in μM |
| --- | --- | --- |
| 1 | 0.39 | 15 |
| 2 | ND | 10 |
| 3 | ND | <5 |
| 4 | ND | <10 |
| 5 | 2.2 | ND |
| 6 | ND | <0.5* |
| 7 | 0.02 | ND |

*EC$_{50}$ determined using MDA-MB-231 cells; EC$_{50}$ values for other compounds determined using MCF-7 cells; ND = not determined.

In another example, a compound's effect on cancer cell migration and invasion were evaluated in a transwell invasion assay. In one such example, addition of compound 6 in a concentration of 5 μM and 10 μM caused an approximately 50% and an approximately 75% reduction, respectively, of invasion of HCC1954 breast cancer cells in the assay.

What is claimed is:

1. A pharmaceutical composition, comprising
a) a compound of formula I or II

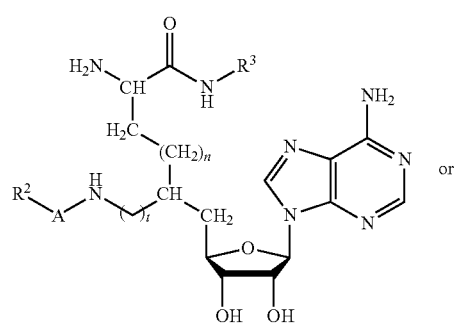

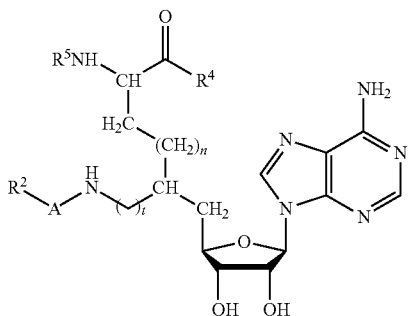

wherein:
A is chosen from a direct bond and a (C$_1$-C$_{10}$)hydrocarbon;
Y is N or CH;
R$^2$ is chosen from —H, and optionally substituted aryl and heteroaryl;
R$^3$ is chosen from
—((CH$_2$)$_m$)aryl substituted with one to three substituents chosen independently from (C$_1$-C$_6$)alkoxy, halo (C$_1$-C$_6$)alkoxy, methylenedioxy, ethylendioxy, (C$_1$-C$_6$)acyl, (C$_1$-C$_6$)alkoxyalkyl, hydroxy(C$_1$-C$_6$)alkyl, hydroxy, carboxy, —C(=O)O—(C$_1$-C$_6$)alkyl], carboxamido, acetoxy, amino, (C$_1$-C$_6$)alkylamino, di(C$_1$-C$_6$)alkylamino, (C$_1$-C$_6$)alkylsulfonylamino, and arylsulfonylamino;
—((CH$_2$)$_m$)heteroaryl optionally substituted with one to four substituents chosen independently from (C$_1$-C$_6$)alkoxy, halo(C$_1$-C$_6$)alkoxy, methylenedioxy, ethylendioxy, (C$_1$-C$_6$)acyl, (C$_1$-C$_6$)alkoxyalkyl, hydroxy(C$_1$-C$_6$)alkyl, hydroxy, carboxy, —C(=O)O—(C$_1$-C$_6$)alkyl], carboxamido, acetoxy, amino, (C$_1$-C$_6$)alkylamino, di(C$_1$-C$_6$)alkylamino, (C$_1$-C$_6$)alkylsulfonylamino, and arylsulfonylamino;
R$^4$ is chosen from —OH, —NH((CH$_2$)$_m$)aryl and —NH((CH$_2$)$_m$)heteroaryl, each said —NH((CH$_2$)$_m$)aryl or —NH((CH$_2$)$_m$)heteroaryl optionally substituted with one to three substituents chosen independently from (C$_1$-C$_6$)alkoxy, halo(C$_1$-C$_6$)alkoxy, methylenedioxy, ethylendioxy, (C$_1$-C$_6$)acyl, (C$_1$-C$_6$)alkoxyalkyl, hydroxy(C$_1$-C$_6$)alkyl, hydroxy, carboxy, —C(=O)O—(C$_1$-C$_6$)alkyl], carboxamido, acetoxy, amino, (C$_1$-C$_6$)alkylamino, di(C$_1$-C$_6$)alkylamino, (C$_1$-C$_6$)alkylsulfonylamino, and arylsulfonylamino;
R$^5$ is

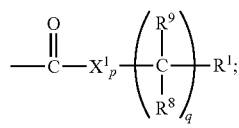

X$^1$ is chosen from O, N, and S(=O)$_2$;
R$^1$ is chosen from hydrogen, C$_1$-C$_{20}$ hydrocarbyl, C$_1$-C$_{20}$ oxaalkyl, C$_1$-C$_{20}$ thiaalkyl, C$_1$-C$_{20}$ azaalkyl, an optionally substituted benzoquinone, an optionally substituted hydrobenzoquinone, and phenyl substituted with at least one oxygenated substituent;
R$^8$ and R$^9$ are chosen independently in each occurrence from H and (C$_1$-C$_3$)alkyl;
m is 0 or an integer from 1 to 10;
n is 1 or 2;
p is an integer from 0 to 1 and q is an integer from 1 to 4, such that the sum of p and q is an integer from 1 to 4; and
t is 0, 1, or 2; and
b) a pharmaceutically acceptable excipient.

2. The pharmaceutical composition of claim 1 wherein Y is N.

3. The pharmaceutical composition of claim 1 wherein A is —CH$_2$—.

4. The pharmaceutical composition of claim 1 wherein R$^2$ is phenyl.

5. The pharmaceutical composition of claim 1 wherein t is 1.

6. The pharmaceutical composition of claim 1 wherein R$^1$ is

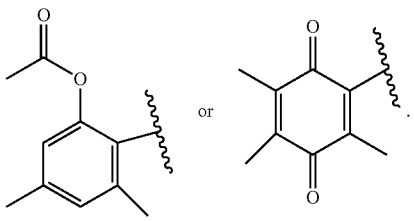 [SMILES: *c1c(C)cc(C)cc1OC(C)=O ; *C1=C(C)C(=O)C(C)=C(C)C1=O]

7. The pharmaceutical composition of claim 1 comprising a compound of Formula II wherein Y is N, A is a direct bond and R$^2$ is benzyl such that R$^2$-A together are benzyl, t is 0, n is 1, R$^5$ is

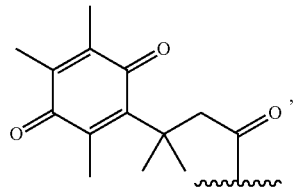 [SMILES: *C(=O)CC(C)(C)C1=C(C)C(=O)C(C)=C(C)C1=O]

and R$^4$ is

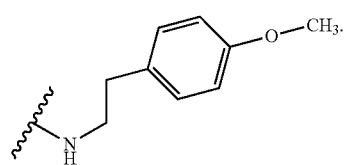 [SMILES: *NCCc1ccc(OC)cc1]

8. The pharmaceutical composition of claim 1 comprising a compound of Formula Ia or IIa

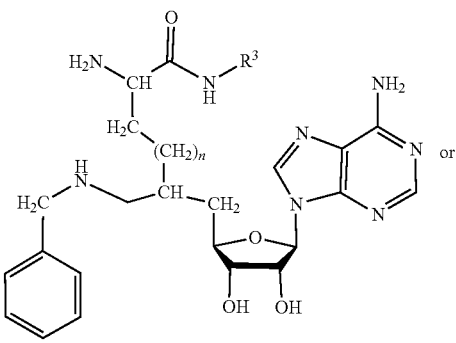

-continued

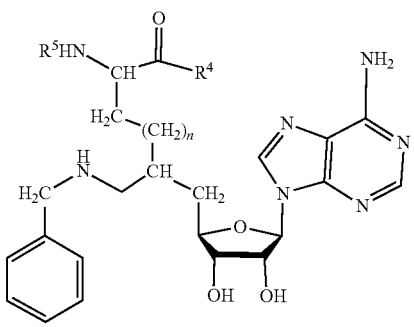

IIa wherein:
R³ is chosen from
—((CH₂)ₘ)aryl substituted with one to three substituents chosen independently from —O((C₁-C₃)alkyl), —O((CH)R⁶ R⁷), methylenedioxy, ethylenedioxy, and halogen; and
—((CH₂)ₘ)heteroaryl optionally substituted with one to four substituents chosen independently from —O((C₁-C₃)alkyl), —O((CH)R₆ R₇), (C₁-C₂₀)hydrocarbon, methylenedioxy, ethylenedioxy, and halogen;
R⁴ is chosen from —OH, —NH((CH₂)ₘ)aryl or —NH((CH₂)ₘ)heteroaryl, each said —NH((CH₂)ₘ)aryl or —NH((CH₂)ₘ)heteroaryl optionally substituted with one to three substituents chosen independently from a halogen, —O((C₁-C₃)alkyl), —O((CH)R₆ R₇), (C₁-C₂₀)hydrocarbon, methylenedioxy, ethylenedioxy, and halogen;
R⁵ is

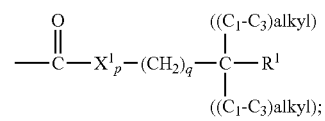

X¹ is chosen from O, N, and S(═O)₂;
R¹ is chosen from hydrogen, C₁-C₂₀ hydrocarbyl, C₁-C₂₀ oxaalkyl, C₁-C₂₀ thiaalkyl, C₁-C₂₀ azaalkyl, an optionally substituted benzoquinone, an optionally substituted hydrobenzoquinone, and phenyl substituted with at least one oxygenated substituent;
R⁶ and R⁷ are independently chosen from H and halogen;
m is 0 or an integer from 1 to 10;
n is 1 or 2; and
p is an integer from 0 to 1 and q is an integer from 0 to 3, such that the sum of p and q is an integer from 0 to 3.

9. The pharmaceutical composition of claim 8 of formula Ia wherein
R³ is —((CH₂)ₘ)phenyl substituted with one to three substituents chosen independently from —O((C₁-C₃)alkyl), —O((CH)R⁶ R⁷), and halogen.

10. The pharmaceutical composition of claim 8 comprising a compound of Formula Ia wherein
R³ is —((CH₂)ₘ)heteroaryl optionally substituted with one to four substituents chosen independently from —O((C₁-C₃)alkyl), —O((CH)R⁶ R⁷) and (C₁-C₂₀)hydrocarbon, wherein said —((CH₂)ₘ)heteroaryl is a nitrogen heteroaryl.

11. The pharmaceutical composition of claim 8 comrpising a compound of formula Ia wherein
R³ is

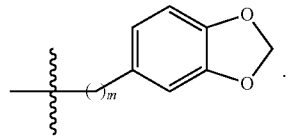

12. The pharmaceutical composition of claim 8 comprising a compound of Formula Ia

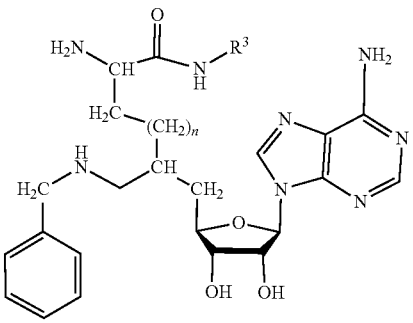

Ia wherein
R³ is —((CH₂)₂)phenyl substituted with one to three substituents chosen independently from —OCH₃, —OCF₂ and halogen; and
n is 2.

13. The pharmaceutical composition of claim 8 comprising a compound of Formula Ia

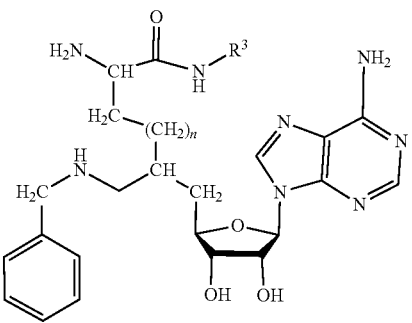

Ia wherein
R³ is chosen from —((CH₂)₂)heteroaryl optionally substituted with one to four substituents chosen independently from halogen, —OCH₃, —OCHF₂, and phenyl; and
n is 2.

14. The pharmaceutical composition of claim 8 comprising a compound of Formula Ia wherein Ia

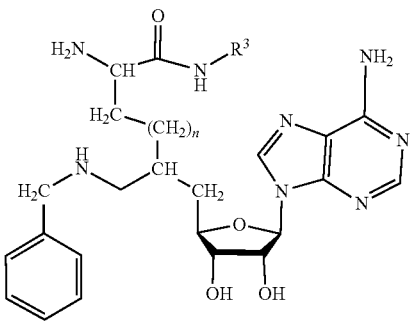

wherein
R³ is

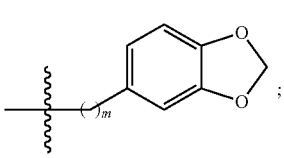

m is 2; and
n is 2.

15. The pharmaceutical composition of claim 8 comprising a compound of Formula IIa wherein
R⁴ is chosen from —OH and —NH((CH₂)$_m$)phenyl, said —NH((CH₂)$_m$)phenyl optionally substituted with one to three substituents chosen independently from halogen, —O((C₁-C₃)alkyl), —O((CH)R⁶ R⁷), and (C₁-C₂₀)hydrocarbon.

16. The pharmaceutical composition of claim 8 comprising a compound of Formula IIa wherein
p is 0; and
R¹ is

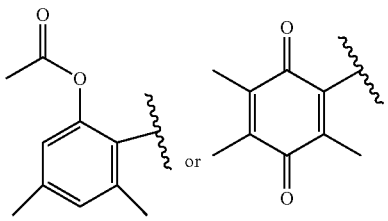

17. The pharmaceutical composition of claim 8 comprising a compound of Formula IIa IIa

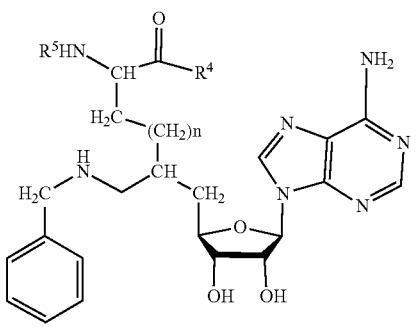

wherein
R⁴ is —OH;
R⁵ is

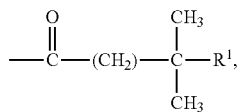

R¹ is

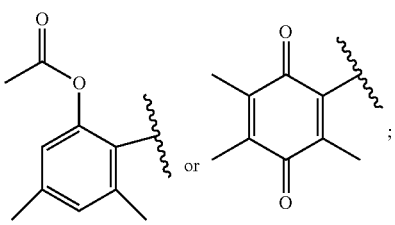

and
n is 2.

18. The pharmaceutical composition of claim 8 comprising a compound of Formula IIa IIa

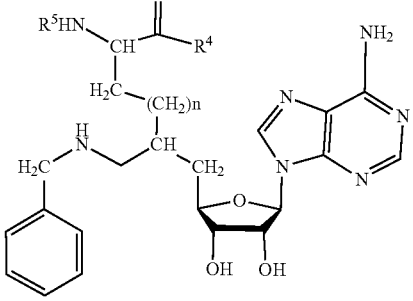

wherein
R⁴ is —NH((CH₂)₂)phenyl optionally substituted with one to three substituents chosen independently from —OCH₃, —OCHF₂, and phenyl;

$R^5$ is

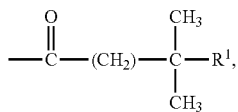

and $R^1$ is

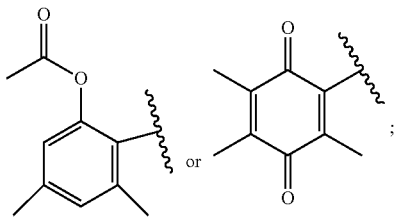

and n is 2.

19. A pharmaceutical composition, comprising
a) a compound of formula III:

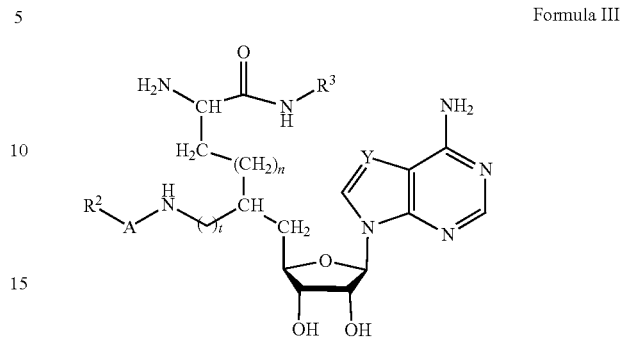

Formula III wherein:
  Y is N;
  A is a direct bond and $R^2$ is benzyl, such that $R^2$-A together are benzyl;
  t is 0;
  n is 1; and
  $R^3$ is —$CH_3$; and
b) a pharmaceutically acceptable excipient.

20. A method of inhibiting the activity of a methyltransferase enzyme comprising contacting methyltransferase enzyme with a pharmaceutical composition according to claim 1.

* * * * *